(12) United States Patent
Etienne et al.

(10) Patent No.: US 11,839,477 B2
(45) Date of Patent: Dec. 12, 2023

(54) EEG ELECTRODE ASSEMBLY

(71) Applicant: Carnegie Mellon University, Pittsburgh, PA (US)

(72) Inventors: Arnelle Etienne, Pittsburgh, PA (US); Harper Weigle, Pittsburgh, PA (US); Pulkit Grover, Pittsburgh, PA (US); Ashwati Krishnan, Pittsburgh, PA (US); Shawn K. Kelly, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 580 days.

(21) Appl. No.: 17/025,715

(22) Filed: Sep. 18, 2020

(65) Prior Publication Data

US 2021/0085206 A1    Mar. 25, 2021

Related U.S. Application Data

(60) Provisional application No. 62/973,199, filed on Sep. 20, 2019.

(51) Int. Cl.
*A61B 5/291* (2021.01)
*A61B 5/00* (2006.01)

(52) U.S. Cl.
CPC ............ *A61B 5/291* (2021.01); *A61B 5/6838* (2013.01); *A61B 2562/125* (2013.01)

(58) Field of Classification Search
CPC ...... A61B 5/291; A61B 5/6814; A61B 5/6838
See application file for complete search history.

(56) References Cited

U.S. PATENT DOCUMENTS

| | | | | |
|---|---|---|---|---|
| 3,469,577 | A * | 9/1969 | Kater | A61N 1/04 600/397 |
| 4,274,418 | A * | 6/1981 | Vesterager | A61B 5/6833 204/415 |
| 4,936,306 | A * | 6/1990 | Doty | A61B 5/377 600/382 |
| 11,311,228 | B1* | 4/2022 | Oakley | A61B 5/0006 |
| 2015/0065838 | A1* | 3/2015 | Wingeier | A61B 5/296 600/397 |
| 2016/0157777 | A1* | 6/2016 | Attal | A61B 5/291 600/383 |
| 2021/0219896 | A1* | 7/2021 | Dauguet | A61B 5/291 |

* cited by examiner

*Primary Examiner* — Eun Hwa Kim
(74) *Attorney, Agent, or Firm* — KDW Firm PLLC

(57) ABSTRACT

The invention comprises an EEG electrode assembly for use in attaching an EEG electrode to the scalp of a subject having coarse, curly and/or long hair, or to subjects having their hair in cornrows, braids, and/or dreadlocks. The invention comprises clips for engaging the hair of the subject, the clips being attached to a central portion for holding electrode in contact with the scalp of the subject when the clips are engaged with the hair of the subject.

15 Claims, 7 Drawing Sheets

EEG ELECTRODE ASSEMBLY

RELATED APPLICATIONS

This application claims the benefit of U.S. Provisional Patent Application No. 62/973,199, filed Sep. 20, 2019, the contents of which are incorporated herein in their entirety.

GOVERNMENT RIGHTS

This invention was made with U.S. Government support under contract CNS1702694, awarded by the National Science Foundation. The U.S. Government has certain rights in this invention.

BACKGROUND OF THE INVENTION

Electroencephalography (EEG) is the most widely used neural inference and imaging technique. EEG involves applying small metal electrodes to the scalp of the subject to detect neural activity. EEG is the gold standard for epilepsy diagnosis and is also used to diagnose traumatic brain injury and to interface computers and machines with the brain. In addition to its incredible and varied uses, EEG is also much more affordable than other inferencing systems, such as MRI.

EEGs may use a series of electrodes to interface a recording apparatus to the subject. For example, in clinical applications, an EEG may typically employ 24 electrodes. The electrodes may be "dry" contact electrodes, which must be held against the scalp of the subject, or may be "wet" electrodes, which are interfaced to the scalp of the subject using a gel as a conductive agent. In current state-of-the-art EEG systems, the contacts of the EEG may be disposed in a cap, akin to a swim cap, which is worn by the subject to hold electrodes near or in contact with the subject's scalp.

One problem with current state-of-the-art EEG systems is that it is possible that the hair of the subject may interfere with the placement of the EEG electrodes, thereby degrading the ability of the EEG electrodes to maintain contact with the subject's scalp. In such cases, it is common for the cap, and thus the electrodes, to be pushed away from the scalp by the subject's hair. Current state-of-the-art EEG systems are therefore unaccommodating to subjects having coarse, curly and/or long hair, or who have their hair in cornrows, braids, and/or dreadlocks, because the existing systems are unable to consistently get reliable contact with the scalps of these subjects. The loss of contact between the subject's scalp and the electrodes due to the aforementioned types of hair pushing the electrodes away from the scalp, significantly reduces the measuring quality of a brain signal.

SUMMARY OF THE INVENTION

The invention described herein resolves this issue by changing the structure by which an electrode is applied to and held to the subject's scalp. The described embodiments can allow for people of all hair types and lengths to have access to quality results from EEGs.

The invention comprises an EEG electrode assembly that can better attach an electrode to the scalp of a subject individual, particularly those having coarse, curly and/or long hair, and also for subject individuals having their hair in cornrows, braids, and/or dreadlocks.

The invention comprises an electrode assembly having a central portion for interfacing with the EEG electrode and a clip portion, attached are the central portion, having one or more clips disposed thereon for engaging the hair of the subject, thereby holding the electrode in close proximity to, if not in actual contact with, the scalp of the subject. The invention therefore provides an improvement in the quality of EEG recording by allowing for better electrode-scalp contact.

DETAILED DESCRIPTION

The invention comprises an EEG electrode assembly that leverages the hair of the subject to make improved contact between the electrode and the scalp of the subject, using the strength of the hair. Because the strength of the hair is used to hold the electrode assembly in place, the electrode can better couple with the scalp of the subject. The invention is particularly effective for subjects having coarse, curly and/or long hair, and also for subject individuals having their hair in cornrows, braids, and/or dreadlocks, which can be used to hold the electrode assembly in place.

Figure 1:
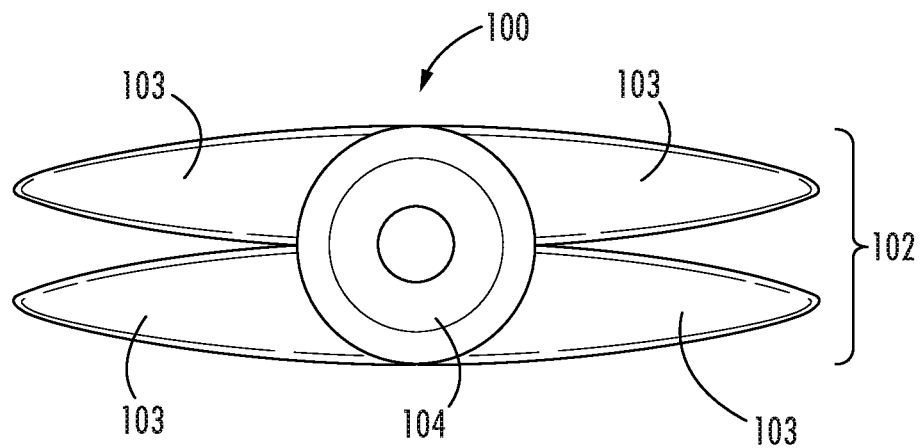
FIG. 1 shows a top view of an exemplary embodiment of the invention.
Figure 2:
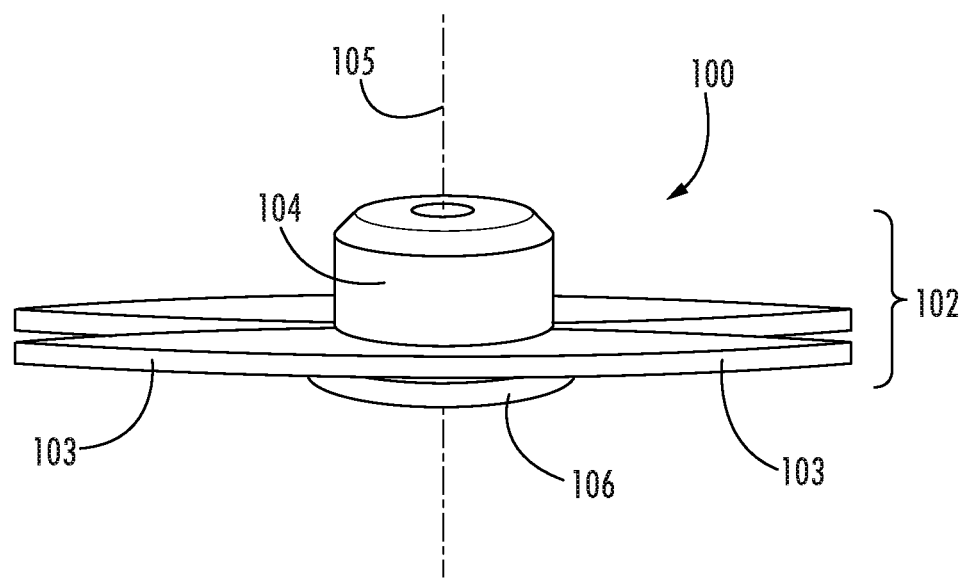
FIG. 2 shows a side perspective view of an exemplary embodiment of the invention.

With reference to FIG. 1 and FIG. 2, in some embodiments, the invention includes an electrode assembly 100 that can attach an electrode (not shown) to the scalp of a subject individual. In some embodiments, the electrode assembly 100 includes a clip portion 102, or a series of clip portions 102, having disposed thereon a plurality of clips, which may be provided in varying configurations. In some embodiments, the electrode assembly 100 includes one or more central portions 104 capable of interfacing with an EEG electrode. The electrode assembly 100 preferably configures the one or more clip portions 102 and the central portion 104 in a manner such that an EEG electrode interfaced with the central portion 104 is held in close proximity to or in contact with the scalp of the subject individual by the one or more clip portions 102 when the one or more clip portions 102 engage the hair of the subject.

To explain the positioning of the one or more clips comprising clip portion 102 with respect to the central portion 104, assume that the central portion 104 has a longitudinal axis 105 extending downward through a hole defined in central portion 104, shown in FIG. 2. In some embodiments, the clip portion 102 may comprise one or more clips 103 which may be positioned approximately orthogonally to the longitudinal axis 105 of the central portion 104. In other embodiments of the invention, the one or more clips 103 may be positioned at varying angles to the longitudinal axis 105 of the central portion 104. In a preferred embodiment of the invention, shown in the drawings, the one or more clips 103 of clip portion 102 are arranged in a plane approximately orthogonal to the longitudinal axis 105 of the central portion 104. In other embodiments, one or more planes containing the one or more clips 103 may be at any angle to the longitudinal axis 105 of the central portion 104. Note that is not necessary that the longitudinal axes of the one or more clips intersect with the longitudinal axis 105 of the central portion 104.

In preferred embodiments of the invention, a first portion of the one or more clips 103 may extend within a plane and a second portion of the one or more clips 103 may extend in the plane in approximately opposing directions from the longitudinal axis 105 of the central portion 104 with respect to each other, such as to provide a downward force from opposing sides of the central portion 104. In yet other embodiments of the invention, the one or more clips 103 may be distributed at varying angles around the longitudinal axis 105 of the central portion 104, regardless of the vertical angle between the one or more clips and the longitudinal axis 105 of the central portion 104.

In certain embodiments, central portion 104 may be configured with a flared or bell-shaped portion 106 which would be placed adjacent the scalp of the subject.

In preferred embodiments of the invention, as shown in FIG. 1 and FIG. 2, the one or more clips 103 comprising clip portion 102 may be shaped such as to have an elongated body having a pointed end, thereby allowing for easy insertion under the hair of the subject. In some embodiments of the invention, the clips 103 may be flattened or may have a varying thickness over the surface of the clip 103. In some embodiments of the invention, the one or more clips 103 may have smooth edges or may have serrated or jagged edges to prevent the clip 103 from slipping out once it is placed under the hair of the subject.

Figure 3:
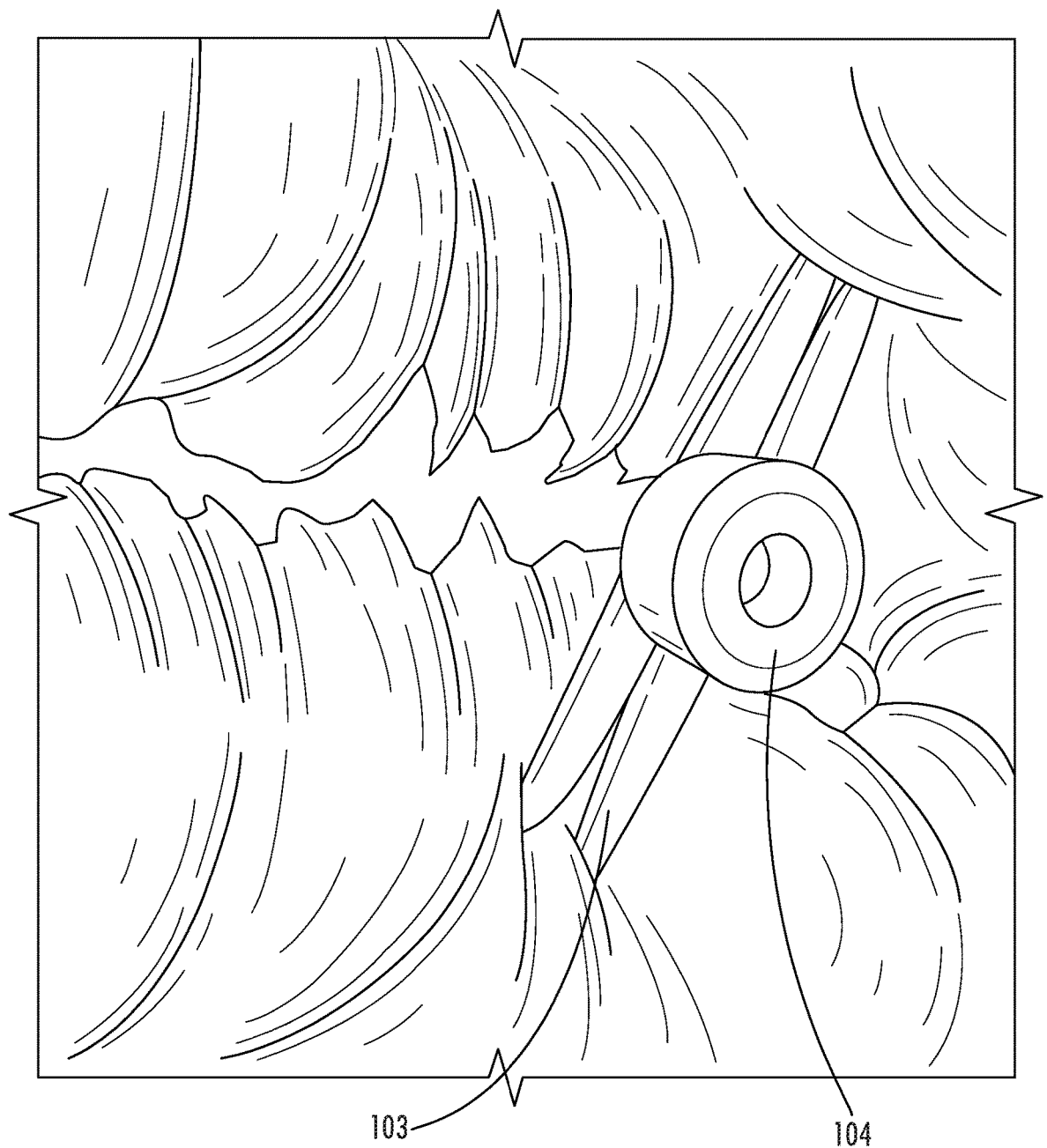
FIG. 3 shows a first view of the device of the present invention in situ on the scalp of a subject mannequin head.
Figure 4:
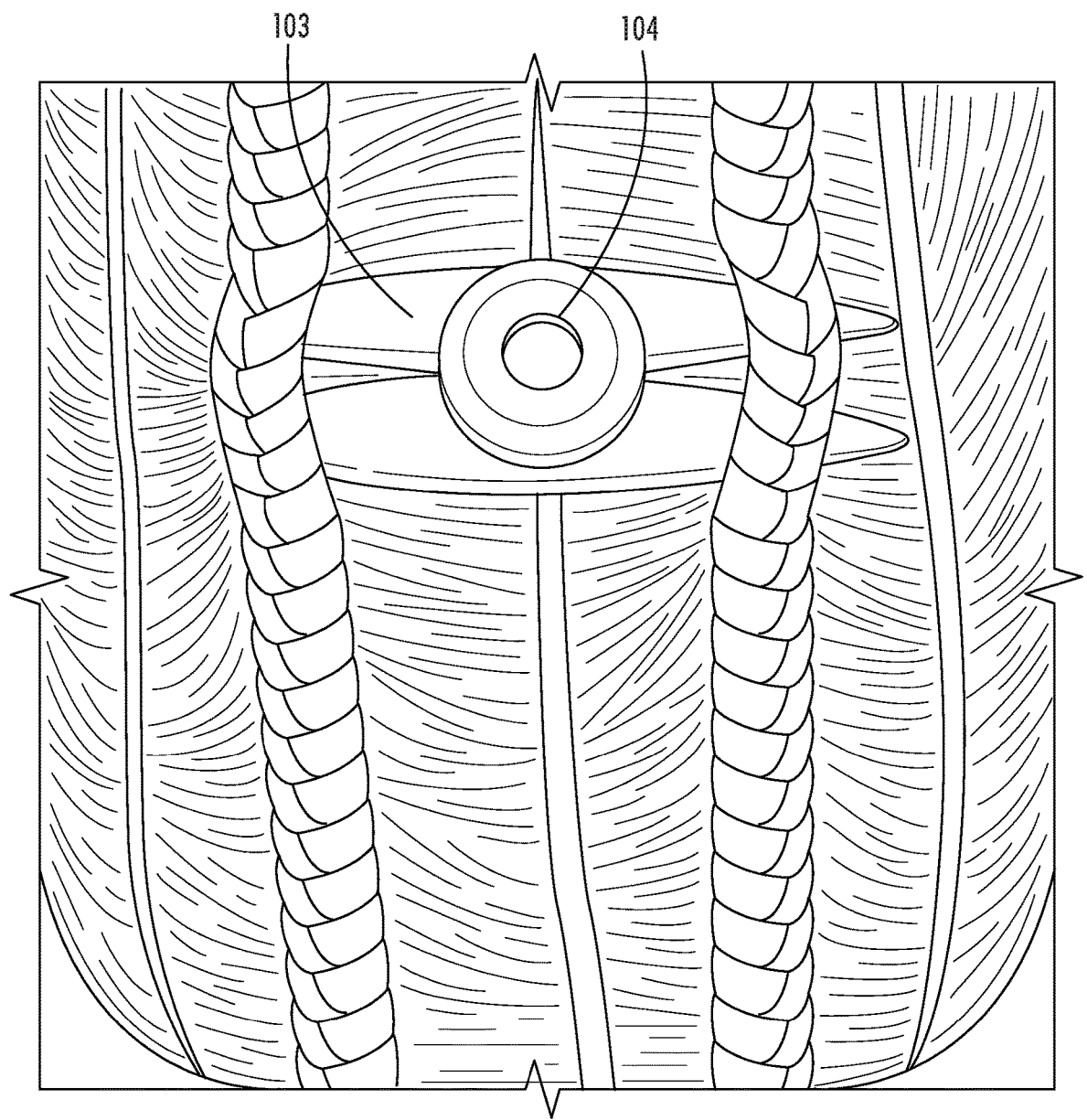
FIG. 4 shows a second view of the device of the present invention in situ on the scalp of a subject mannequin head.

FIG. 3 and FIG. 4 show an exemplary embodiment of the invention in situ in the hair of a subject. FIG. 3 shows the use of parted and secured hair as the binding agent for the one or more clips 103. FIG. 4 shows the use of hair arranged in cornrows or braids as the binding agent for the one or more clips 103. The invention helps to maintain the position of the electrode such that the electrode is properly interfaced with the scalp of the subject and to and restrict electrode mobility by using the downward force of the hair. The described clip portion 102 leverages the strength of hair to firmly push the central portion 104, containing the interface to the electrode or the electrode itself, to the scalp of the subject.

Figure 5A:
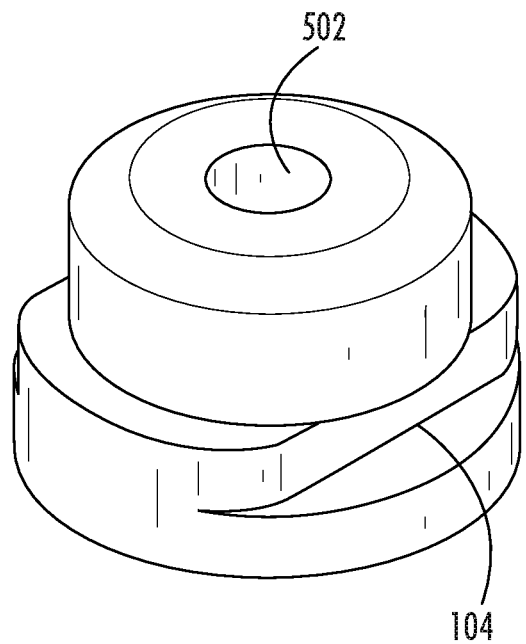
FIGS. 5(A)-5(B) illustrates an exemplary embodiment of a portion of the electrode assembly which holds an EEG electrode or an electrode interface.

FIG. 5(A) shows one embodiment of the central portion 104 of electrode assembly 100. Central portion 104 is configured with recess 502. In certain embodiments, an EEG electrode made be disposed within recess 502. In some embodiments, the electrode disposed within recess 502 may be a dry contact electrode which extends through recess 502 such as to be held in contact with the scalp of the subject by electrode assembly 100. In other embodiments utilizing a wet contact, the electrode made comprise a snap attachment disposed near the top of central portion 104 and a gel which fills recess 502 and contacts the scalp of the subject. The snap attachment may be of the type typically fitted to a silver/silver chloride tab used by EEG or EKG devices to accept the connection of a wired interface to the recording device. In such embodiments, the gel may be considered to be a part of or the entirety of the electrode.

In embodiments using a wet contact, the flared portion 106 shown in FIG. 2 may be present on central portion 104 such as to contain the gel when the electrode assembly 100 is pressed against the scalp of the subject, such as to prevent the gel from one electrode assembly 100 from interfering with gel from other electrode assemblies. In embodiments using a dry contact, the flared portion 106 may be absent.

Figure 5B:
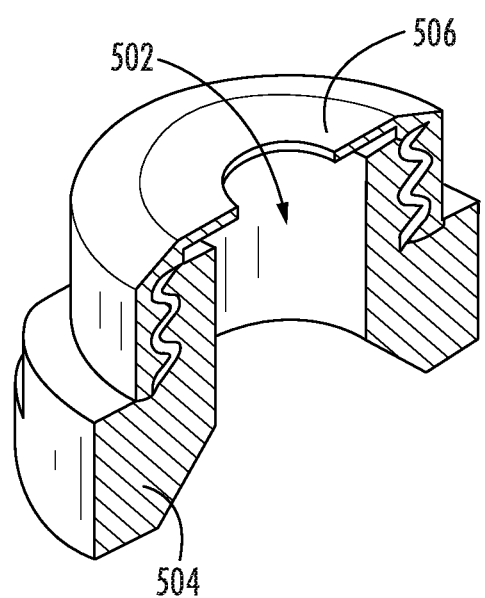

Although, in the exemplary embodiment described herein, recess 502 of central portion 104 is circular, it should be realized that recess 502 could be of any shape. FIG. 5(B) shows a cutaway view of central portion 104. In some embodiments, central portion 104 may comprise body portion 504 and cap portion 506 which may be joined by a threaded interface or, in other embodiments, by any type of friction interface which may hold body portion 504 and cap portion 506 in a locked configuration with respect to each other. To place an EEG electrode or a silver/silver chloride snap within central portion 104, body portion 504 and cap portion 506 may be separated and the electrode or electrode interface may be placed in recess 502 and locked in place within central portion 104 when body portion 504 and cap portion 506 are joined together.

Figure 6:
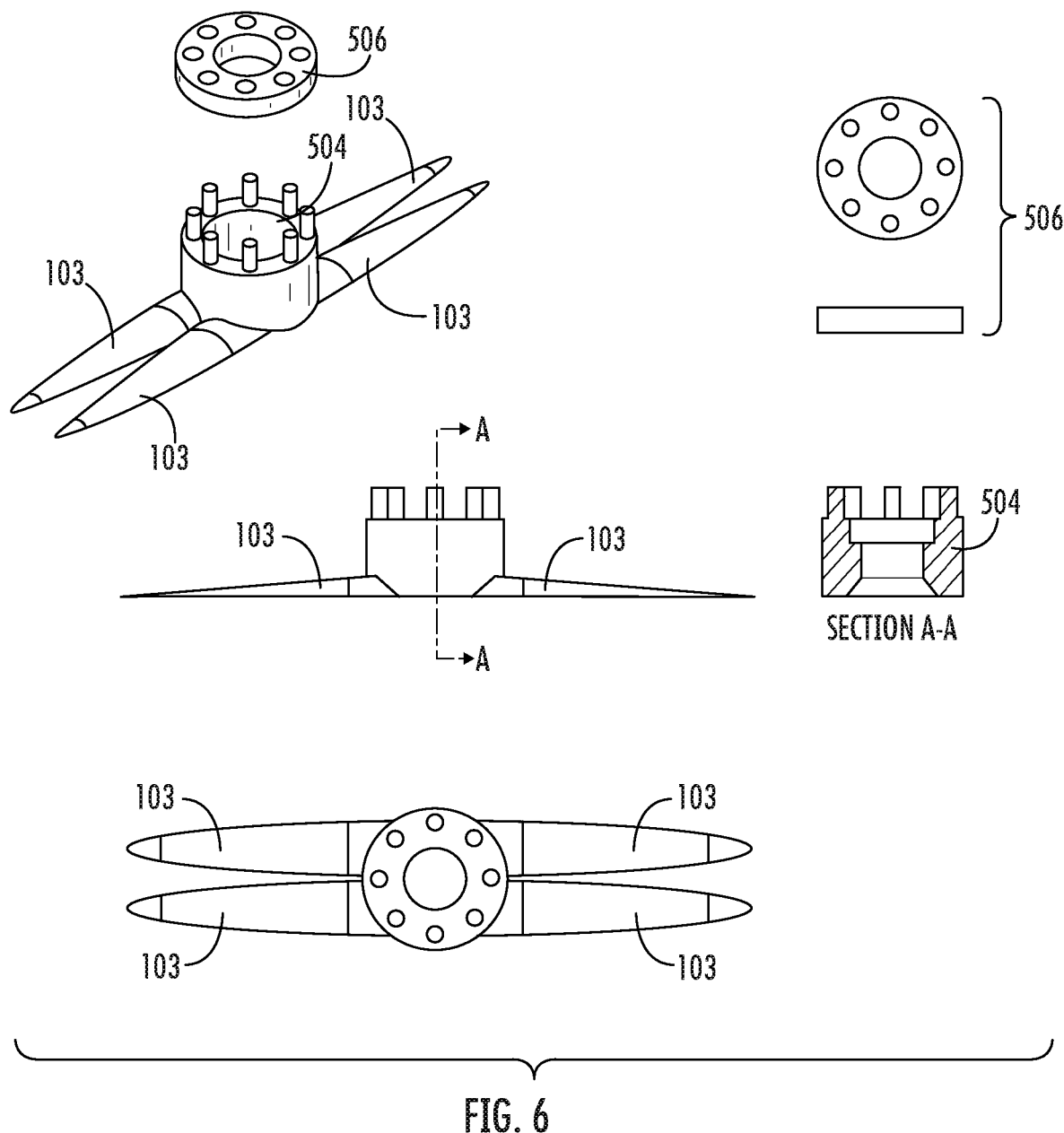
FIG. 6 illustrates a unitary view of an exemplary embodiment of the invention showing the portion in which the EEG electrode is disposed and the portion for engaging the hair of the subject.

FIG. 6 shows a second possible embodiment of the central portion 104 in which body portion 504 is configured with a plurality of pegs which may be received in holes disposed in cap portion 506 to hold body portion 504 and cap portion 506 together when an EEG electrode or electrode interface is placed within recess 502. FIG. 6 also illustrates the attachment of central portion 104 to clip portion 102. In certain embodiments, body portion 504 of central portion 104 may be manufactured integrally with clip portion 102, while cap portion 506 of central portion 104 may be manufactured as a separate piece. Alternatively, body portion 504 of central portion 104 may be manufactured separately from clip portion 102 and joined with clip portion 102 via any means well known in the art, for example, by an adhesive.

The electrode assembly 100 may be manufactured by any one of a number of various additive manufacturing methods. For example, all or some of the components of electrode assembly 100 may be manufactured by 3D printing. In other embodiments, one or more components of electrode assembly 100 may be laser cut during or after 3D printing. In some embodiments, one or more components of electrode assembly 100 may be manufactured using an injection molding process.

In some embodiments, one or more components of electrode assembly 100 may be manufactured from a polymeric material. Examples of suitable polymeric materials may include, but are not limited to, polyethylene, photopolymer resin, polyester, polycarbonate, polyamide, polypropylene, polystyrene, polyurethane, polyvinyl chloride, polyvinylidene chloride, acrylonitrile butadiene styrene, polyepoxide, polymethyl methacrylate, polytetratluoroethylene, phenol formaldehyde, melamine formaldehyde, urea-formaldehyde, polyetheretherketone, maleimide, polyetherimide, polyimide, plastarch material, polylactic acid, furan, silicone, polysulfone, polydiketoenamine, and/or any combination thereof.

In another embodiments, all or portions of electrode assembly 100 may be composed of a metal. For example, clip portion 102 may be composed of a metal while central portion 104 may be composed of a polymeric material to preclude interference with the electrode.

In some embodiments, electrode assembly 100 may include a clip portion 102 having multiple clips 103 which may be disposed in any manner around central portion 104. It should be realized that, while the exemplary embodiment described herein and illustrated in the figures shows a clip portion 102 configured with two clips 103 on opposite sides of central portion 104, clip portion 102 may contain any number of clips 103 which may be arranged in any configuration around central portion 104. In addition, clips 103 may be of any suitable shape.

In some embodiments, central portion 104 may receive an electrode composed of, at least in part, a metal. In some embodiments, central portion 104 may receive EEG electrodes of varying shapes, including, for example, an EEG electrode in the shape of a metal disc or cup. Recess 502 may be of any suitable shape and configured to accept the any particular EEG electrode, including electrodes comprising a gel disposed within recess 502. Note that the use of the term "gel" herein should be interpreted to include conductive gels, conductive pastes, conductive foams, conductive sponges and/or any other suitable material forming a wet contact between the subject and the electrode interface to the recording device.

Figure 7:
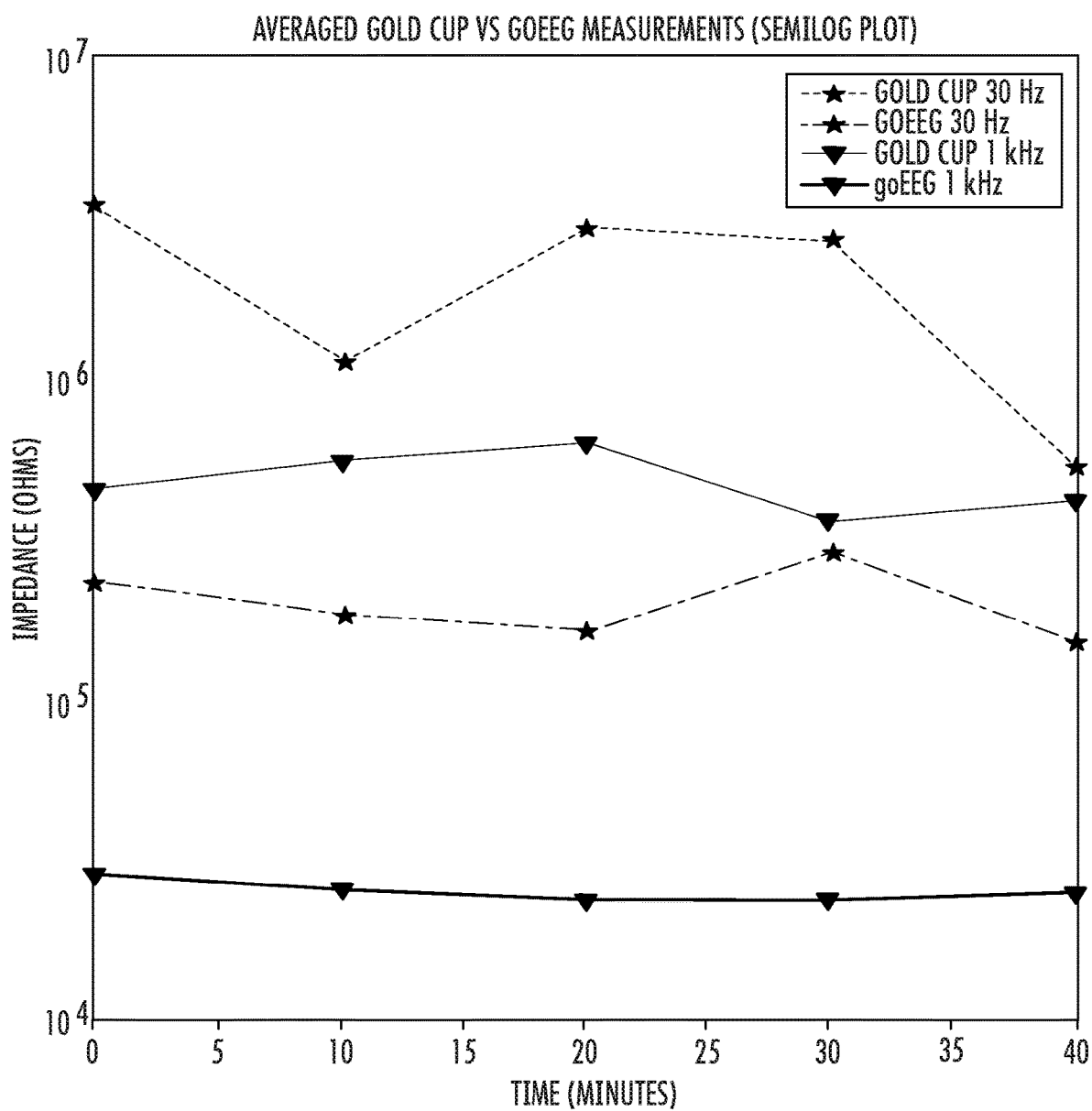
FIG. 7 is a graph showing data obtained from experiments on the described invention. The graph shows that the invention provides a lower impedance compared to a leading EEG cap due to the ability of the invention attach firmly to an individual's scalp, thereby holding the EEG electrode against the scalp.

FIG. 7 is a graph showing data obtained from experiments involving the invention described herein. The graph shows that the invention has a lower impedance compared to a leading EEG cap due to the ability of the invention to attach firmly to the scalp of the subject. The invention and the prior art cap were both tested at 30 Hz and 1 kHz frequency levels for 0-40 minutes. Because the invention has a lower impedance compared to a leading prior art EEG cap, an electrode or electrodes can better record the brain waves of an individual.

Figure 8:
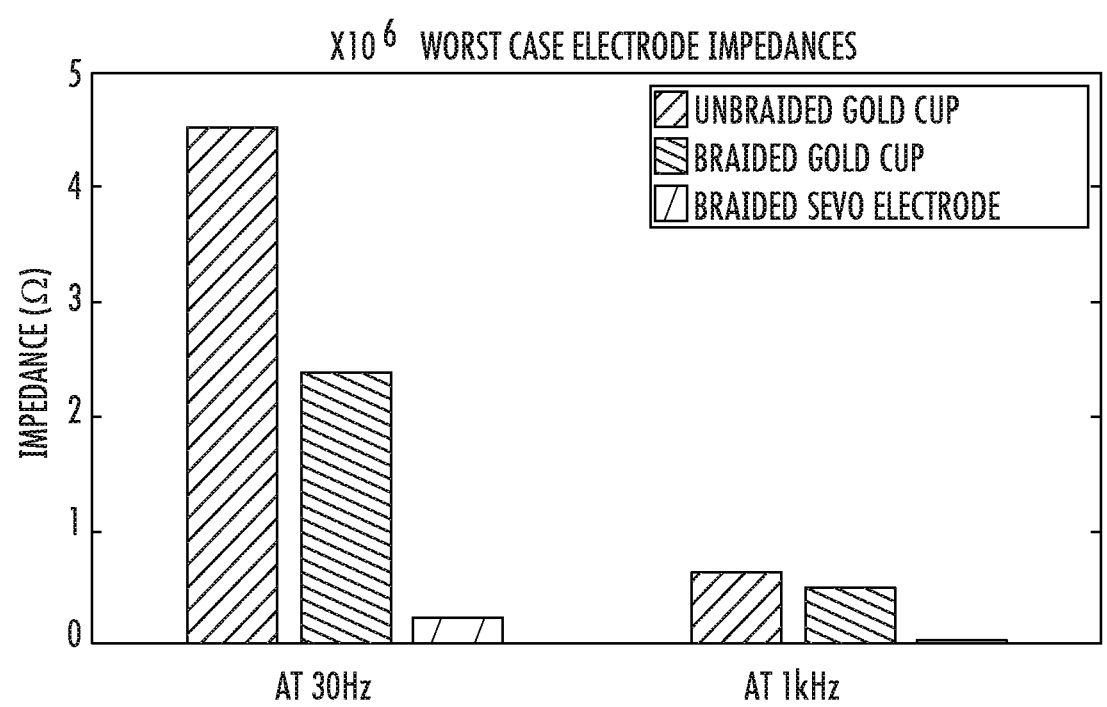
FIG. 8 is a graph showing measured impedances for various types of electrodes.

FIG. 8 is a graph showing measured impedances, recorded at their highest average value across time. The y-axis is linear in scale. Braiding and using Sevo electrodes results in lower electrode-skin impedance. The graph shows the values at 30 Hz and 1000 Hz as that is the frequency at which an EEG is typically recorded and the standard frequency for which impedance is reported, respectively.

The invention described herein is not meant to be limited in any way by the described exemplary embodiments, which are provided solely for the purpose of illustrating various aspects of the invention. In addition, any sizes, dimensions, configurations, materials or methods of manufacture described herein or shown in the drawings are exemplary only and are not meant to limit the invention in any way. Variations of any aspect of the invention are intended to be within the scope of the invention. As would also be realized by one of skill in the art, the invention described herein is not limited to use with EEG electrodes but may be used with any apparatus requiring close contact with the scalp (or any other body part) of the subject. As such, the scope of the invention is set forth in the claims which follow.

The invention claimed is:

1. A device for positioning an electrode with respect to a subject comprising:
   a body comprises:
      an elongate body portion;
      a flared end extending from the elongate body portion and being adapted to physically contact the scalp; and
      a recess extending through the elongate body portion and the flare end to receive the electrode;
   a cap detachably connected to the elongate body portion and adapted for enclosing the electrode within the recess;
   one or more clips disposed between the flared end and the cap and extending perpendicular to a longitudinal axis of the body such that the cap is configured to rigidly hold the one or more clips against the flared end when the one or more clips is engaged with hair of the subject.

2. The device of claim 1, wherein a first portion of the one or more clips extend from one side of the longitudinal axis of the body and wherein a second portion of the one or more clips extend from an opposite side of the longitudinal axis of the body and further wherein the one or more clips extending from opposite sides of the body portion are rigidly attached to the body.

3. The device of claim 1, wherein the one or more clips have a substantially flat profile.

4. The device of claim 2 wherein the one or more clips have a tapered end to facilitate the placement of the one or more clips under the hair of the subject.

5. The device of claim 2 wherein the one or more clips have a serrated edge to hold the clips under the hair of the subject.

6. The device of claim 1, wherein the cap attaches to the body using interconnecting threads.

7. The device of claim 1, wherein the cap attaches to the body using a friction fit.

8. The device of claim 1, wherein the one or more clips is composed of a polymeric material.

9. The device of claim 1, wherein the body is composed of a polymeric material.

10. The device of claim 1, wherein the cap is composed of a polymeric material.

11. The device of claim 1, wherein the one or more clips, the body, and the cap are composed of a polymeric material.

12. The device of claim 1, wherein the one or more clips, the body, and the cap are manufactured via an injection molding process.

13. The device of claim 1, wherein the one or more clips, the body, and the cap are manufactured via a 3-dimensional (3D) printing process.

14. A device for positioning an electrode with respect to a subject comprising:
   a body comprises:
      a central opening therethrough to receive the electrode;
      a first end being adapted to physically contact the scalp;
      at least one clip extending from the body in a direction perpendicular to the central opening and configured to engage hair of the subject; and
      a second end comprising a plurality of pegs; and
   a cap comprising a plurality of holes mating with the plurality of pegs when engaged with the second end of said body.

15. The device of claim 14, wherein the at least one clip is formed integrally with the body.

* * * * *